(12) United States Patent
Roach et al.

(10) Patent No.: US 8,481,583 B2
(45) Date of Patent: Jul. 9, 2013

(54) COMBINATION OF ALPHA-2 RECEPTOR AGONIST (CLONIDIN) AND ANTI-MUSCARINIC AGENT (OXYBUTYNIN) FOR THE TREATMENT OF SIALORRHOEA

(75) Inventors: Alan Geoffrey Roach, Abingdon (GB); Paul Goldsmith, Abingdon (GB)

(73) Assignee: Orient Pharma (Samoa) Co., Ltd., Apia (WS)

( * ) Notice: Subject to any disclaimer, the term of this patent is extended or adjusted under 35 U.S.C. 154(b) by 446 days.

(21) Appl. No.: 12/279,217

(22) PCT Filed: Feb. 12, 2007

(86) PCT No.: PCT/GB2007/050057
§ 371 (c)(1),
(2), (4) Date: Dec. 18, 2008

(87) PCT Pub. No.: WO2007/093824
PCT Pub. Date: Aug. 23, 2007

(65) Prior Publication Data
US 2009/0221659 A1 Sep. 3, 2009

(30) Foreign Application Priority Data

Feb. 13, 2006 (GB) .................................. 0602855.9
Feb. 13, 2006 (GB) .................................. 0602857.5

(51) Int. Cl.
*A61K 31/4168* (2006.01)
*A61P 7/00* (2006.01)

(52) U.S. Cl.
USPC ........................................................ 514/401

(58) Field of Classification Search
USPC ........................................................ 514/401
See application file for complete search history.

(56) References Cited

U.S. PATENT DOCUMENTS

| | | | | |
|---|---|---|---|---|
| 4,312,879 A | * | 1/1982 | Lal | 514/392 |
| 5,578,295 A | * | 11/1996 | Francis et al. | 424/57 |
| 6,545,046 B2 | | 4/2003 | Sherratt et al. | |

FOREIGN PATENT DOCUMENTS

| WO | WO 9963997 | * | 12/1999 |
|---|---|---|---|
| WO | WO 01/08681 A1 | | 2/2001 |
| WO | WO-2007-093824 | | 8/2007 |
| WO | WO-2008-059190 | | 5/2008 |

OTHER PUBLICATIONS

Cree et al. Psychiatric Bulletin (2001), 25 114-116.*
Loesche et al. J. Am. Geriatric Soc. (1995) 43(4) 401-7 Abstract only.*
Bagheri, H. et al., "Effect of 3 weeks treatment with yohimbine on salivary secretion in healthy volunteers and in depressed patients treated with tricyclic antidepressants," *British Journal of Clinical Pharmacology*, Dec. 1992, vol. 34, No. 6, pp. 555-558, Abstract, Ref. 4.
Bagheri, H. et al., "Pharmacokinetic study of yohimbine and its pharmacodynamic effects on salivary secretion in patients treated with tricyclic antidepressants," *British Journal of Clinical Pharmacology*, Jan. 1994, vol. 37, No. 1, pp. 93-96, Abstract, Ref. 3.
Bagheri, H. et al., "A comparative study of the effects of yohimbine and anetholtrithione on salivary secretion in depressed patients treated with psychotropic drugs," *European Journal of Clinical Pharmacology*, 1997, vol. 52, No. 5, pp. 339-342, Abstract, Ref. 2.
Bagheri, H. et al., "A study of salivary secretion in Parkinson's disease," *Clin. Neuropharmacology*, Jul.-Aug. 1999, vol. 22, No. 4, pp. 213-215, Abstract, Ref. 5.
Chatelut, E. et al., "Yohimbine increases human salivary secretion.", Abstract, Ref. 7.
Krishnan, O., "Clozapine-Induced Sialorrhea Treated With Sublingual Ipratropium Spray: A Case Series," *Journal of Clinical Psychopharmacology*, Feb. 2004, vol. 24, No. 1.
Freudenreich, O., "Drug-induced sialorrhea," *Drugs of Today*, 2005, vol. 41, No. 6, p. 411.
Girolami, J.P. et al., "Yohimbine increases submaxillary kallikrein release into the saliva in dogs: evidence for alpha 2-adrenoceptor-mediated inhibition of cholinergic pathways," *British Journal of Pharmacology*, Feb. 1991, vol. 102, No. 2, pp. 351-354, Abstract, Ref. 1.
Grabowski, J., "Clonidine Treatment of Clozapine-Induced Hypersalivation," *Journal of Clinical Psychopharmacology*, Feb. 2002, vol. 12, No. 1, p. 69-70.
Montastruc, P. et al., "Effects of yohimbine on submaxillary salivation in dogs," *British Journal of Pharmacology*, Sep. 1989, vol. 98, No. 1, pp. 101-104, Abstract, Ref. 6.
Praharaj, Samir Kumar et al., "Is clonidine useful for treatment of clozapine-induced sialorrhea?" *Journal of Psychopharmacology*, Jul. 2005, vol. 19, No. 4, pp. 426-428.
Rogers, Donald P. et al., "Therapeutic options in the treatment of clozapine-induced sialorrhea," *Pharmacotherapy*, Sep. 2000, vol. 20, No. 9, pp. 1092-1095.
EP1218773.8 Search Report dated Oct. 18, 2012.
Chancellor et al., "A comparison of the effects on saliva output of oxybutynin chloride and tolterodine tartrate," Clinical Therapeutics 23: 753-760 (2001).
Corrigan et al., Clozapine-induced hypersalivatio and the alpha 2 adrenoreceptor, Br. J. Psychiatry 167: 412 (1995).
Davydov et al., "Clozapine induced hypersalivation," Ann Pharmacother 35: 662-665 (2000).
Levinson et al., "Stability of an extemporaneously compounded clonidine hydrochloride oral liquid," Am. J. Hosp. Pharm 49: 122-125 (1992) (Abstract only).
Indian App. No. 6924/DELNP/2008 Examination Report dated Oct. 17, 2012.
Calderon et al., "Potential use of ipatropium bromide for the treatment of clozapine-induced hypersalivation: a preliminary report." Int. Clin. Psychopharmacol., 15, 49-52 (2000).

(Continued)

*Primary Examiner* — Shirley V Gembeh

(74) *Attorney, Agent, or Firm* — Wilson, Sonsini, Goodrich & Rosati

(57) ABSTRACT

An alpha2 adrenoreceptor agonist eg. clonidine, brimonidine, monoxidine, lofexidine is useful for the treatment of sialorrhoea, administered by the paraungual, sublingual or buccal route. The patient to be treated is also given an anti-muscarinic agent eg. oxybutynin, glycopyrrolate, ipratropium.

6 Claims, 2 Drawing Sheets

OTHER PUBLICATIONS

Sharma, "Intraoral Application of Atropine Sulfate Ophthalmic Solution for Clozapine-Induced Sialorrhea." Ann. Pharmacother., 38, 1538 (2004).

Hyson, et al. "Sublingual Atropine for Sialorrhea Secondary to Parkinsonism: A Pilot Study." Mov. Disorders, 17(6), 1318-1320 (2002).

Kohler, et al. "A Quantitative Test for Xerostomia: The Saxon Test, an Oral Equivalent of the Schirmer Test." Arthritis Rheum. 28, 1128-32 (1985).

Stevens, et al., "Use of the Saxon Test as a Measure of Saliva Production in a Reference Population of Schoolchildren." Am. J. Diseases Children, 144: 570-571 (1990).

* cited by examiner

COMBINATION OF ALPHA-2 RECEPTOR AGONIST (CLONIDIN) AND ANTI-MUSCARINIC AGENT (OXYBUTYNIN) FOR THE TREATMENT OF SIALORRHOEA

This application is a National Stage Application of international Application Number PCT/GB2007/050057, filed Feb. 12, 2007; which claims priority to Great Britain Patent Application No. 0602857.5, filed Feb. 13, 2006 and Great Britain Application No. 0602855.9, filed Feb. 13, 2006, all of which are incorporated herein in their entirety.

FIELD OF THE INVENTION

This invention relates to a drug combination and its use in the treatment of sialorrhoea.

BACKGROUND OF THE INVENTION

Patients with severe neurological dysfunction such as motor deficits (e.g. cerebral palsy, peripheral neuromuscular disease, facial paralysis, Parkinson's disease, severe mental retardation, and other conditions such as stroke and esophageal cancer) suffer from sialorrhoea (or drooling), which is the unintentional loss of saliva and other oral contents from the mouth. Drooling is often found in individuals with neurological dysfunction. For example, socially significant drooling occurs in approximately 10% of patients with cerebral palsy. Persistent drooling beyond the ages of 3 or 4 years is considered abnormal drooling. Sialorrhoea results from either a hypersecretion of saliva or an impaired ability to swallow; the latter is a particular problem in patients with motor dysfunction.

Drooling causes impairment of speech, feeding and swallowing problems and aspiration. Control of drooling is important in preventing choking and gagging in persons with posterior drooling. Persons who are motor-impaired can use the many new electronic assistance aids to communicate, navigate and provide more integration and self-sufficiency in everyday life. Unfortunately for those who drool, many of the aids are controlled through the mouth or facial manipulations. The drooling may cause social isolation and inability to use the new devices.

Not only is the drooling annoying and limiting for the person with sialorrhoea, there are problems for the caregivers. Carers must clean and control the drooling, and remove the drool from the body, clothes and surrounding equipment of the drooler. Additionally, carers must be very careful about exposure to bodily fluids such as drool.

Thus, it is recognized that sialorrhoea requires medical attention. Current treatment includes administration of anticholinergic agents such as glycopyrrolate and scopolamine, botulinum toxin injections and surgery.

Where an anti-sialorrheic effect (reduced saliva secretion) is required, it is appropriate neither to completely impair secretion nor to prevent saliva production in response to food etc. It may be possible to reduce the amount of saliva produced by administering an anticholinergic agent, as demonstrated by the positive effects of glycopyrrolate (tablets) and scopolamine (dermal patch). Although glycopyrrolate is a quaternary ammonium compound with restricted access to the CNS, it is not well tolerated by around 20-25% of patients. Likewise, scopolamine is reasonably tolerated for a few days, but many systemic side-effects are encountered. The saliva produced following administration of glycopyrrolate or scopolamine is extremely thick and as such is unpleasant.

Clonidine is an $\alpha 2$-adrenoceptor agonist and is primarily used clinically as an antihypertensive agent. It acts within the central nervous system to reduce sympathetic nervous tone to the periphery. Besides lowering blood pressure and heart rate, clonidine also causes pronounced sedation and dry mouth. Clonidine has been shown to be effective in reducing sialorrhoea induced by clozapine (Grabowski, 1992, J. Clin. Psychopharmacol., 12, 69-70; Praharaj et al., 2005, J. Psychopharmacol., 19, 426-428). Clonidine (0.15 mg) has been given per os to 17 Parkinson's patients and found to significantly reduce sialorrhoea. Four of the 17 patients experienced side-effects.

Clonidine is one of many imidazole-type compounds that are used clinically to treat conditions such as hypertension, sedation as an adjunct to anaesthesia (premedication), muscle spasm (spasticity), and withdrawal symptoms of opiate and alcohol abuse. Examples of other such compounds are rilmenidine, dexmedetomidine, tizanidine, moxonidine and lofexidine. All produce their clinical effects by stimulating $\alpha 2$-adrenoceptors in the brain and cause sedative side-effects and dry mouth.

Sialorrhoea can be a side-effect of the administration of certain drugs. For example, clozapine-induced sialorrhoea has been treated with some success with solutions of the non-selective muscarinic receptor antagonist ipratropium, a quaternary derivative of atropine, given either sublingually or intranasally (O. Freudenreich et al., 2004, J. Clin. Psychopharmacol., 24, 98-100; J. Calderon et al., 2000, Int. Clin. Psychopharmacol., 15, 49-52). Freudenreich et al. (2004) gave ipratropium nasal spray (0.03-0.06%) sublingually to 8 patients receiving clozapine and who suffered from excessive drooling. After several weeks of use, a full response was reported in 2 patients and a partial response (symptoms controlled for 2-8 hours) in 5 patients, while 1 patient was a non-responder. One drawback with the ipratropium solution is its bitter taste. In addition, an ophthalmic solution of atropine given sublingually was found to reduce clozapine-indiced sialorrhoea (A. Sharma et al., 2004, Ann. Pharmacother., 38, 1538). In a small case study, ophthalmic atropine solution was given sublingually to patients with Parkinson's disease and significant decline in saliva production was recorded. However, 2 of the 7 patients suffered hallucinations (H. C. Hyson et al., 2002, Mov. Disorders, 17, 1318-1320). Atropine is a non-selective muscarinic antagonist that exhibits significant central nervous system side-effects. The use of non-selective muscarinic antagonists that extensively enter the brain and produce undesirable side-effects should be avoided, particularly in patients with Parkinson's disease (PD).

Another class of known drugs is of anti-muscarinic agents. A new generation of anticholinergic muscarinic antagonists is being developed for indications such as urinary incontinence, overactive bladder, irritable bowel syndrome or COPD. These compounds include tolterodine, darifenacin, solifenacin, zamifenacin, Ro-3202904 (PSD-506), oxybutynin, trospium, revatropate and tiotropium.

Patients with PD are more prone to confusion and hallucinations, particularly as their disease progresses. Also their blood-brain barrier may become more leaky. They are thus much more prone to worsening confusion and hallucinations when given an anticholinergic agent. Sleep problems are also extremely common in PD. $\alpha 2$ agonists promote sleep and therefore are undesirable in PD. Furthermore, in the more elderly population, cardiovascular problems are much more common, as is, particularly in males, bladder outflow obstruction. $\alpha 2$ agonists would be undesirable for the former and anti-muscarinic agents for both.

SUMMARY OF THE INVENTION

The present invention is based on the finding that a combination of an anti-muscarinic agent and an α2-adrenoceptor agonist is useful in the treatment of sialorrhoea. The combination can have an improved effect and/or reduced side-effects. The two agents may be administered together, in a single composition, or simultaneously, or sequentially.

Further, if the agonist does not cross the blood-brain barrier or is administered in such a way that it does not readily enter the CNS or is given at such concentration that undesired central effects are not seen, it might be expected to reduce salivary flow by stimulating the negative feedback of α2-adrenoceptors on cholinergic and sympathetic nerves supplying the salivary glands, without producing centrally mediated side-effects such as hypotension and sedation. Therefore, the α2-adrenoceptor agonist at least is preferably administered by the paraungual, sublingual or buccal route.

DESCRIPTION OF PREFERRED EMBODIMENTS

Figure 1:
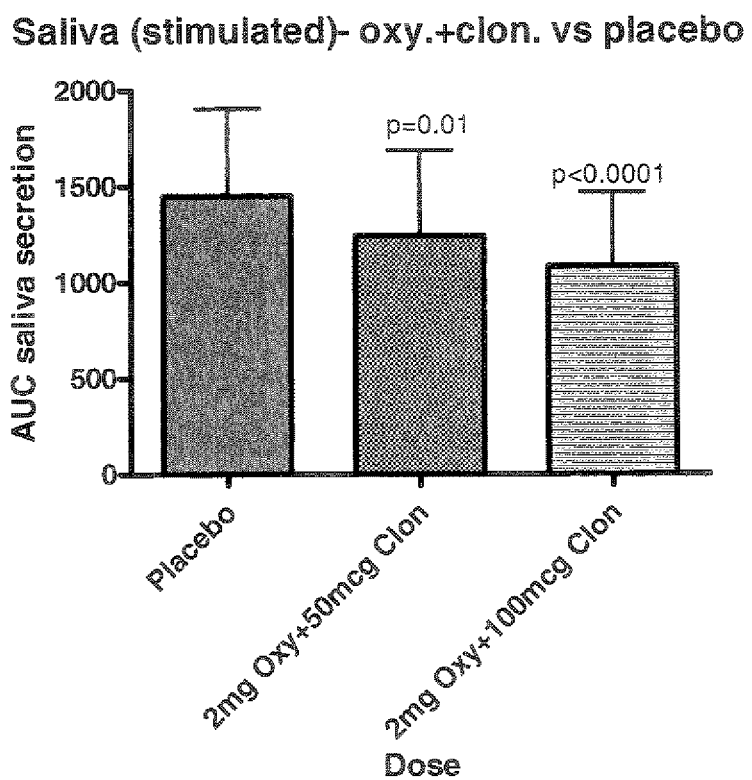
FIGS. 1 and 2 are each bar charts of saliva secretion following drug administration, showing the results of experiments reported below.

Preferred α2-adrenoceptor agonists for use in the invention are clonidine, apraclonidine, brimonidine, rilmedinide, dexmedetomidine, tizanidine, monoxidine and lofexidine. Preferred anti-muscarinic agents for use in the invention are tolterodine, darifenacin, solifenacin, zamifenacin, oxybutynin, trospium, revatropate, tiotropium and Ro-3202904 (PSD-506).

Each active agent may be used, according to the invention, in any appropriate form, e.g. as a salt, hydrate or prodrug. If a chiral molecule, it may be used as a racemate, as a non-racemic mixture or as a substantially single enantiomer.

In general, each active agent may be administered in any suitable formulation, by paraungual, sublingual or buccal route. It is preferably formulated as a gum, spray, pastille, lozenge or dispersible tablet.

The respective active agents may be formulated together in a single dosage form. Alternatively, they may be formulated separately and packaged together, or they may be administered independently. In certain cases, a patient may be receiving one drug for the treatment of another indication; this invention then comprises administering the other drug.

Compositions for use in the invention may be formulated in a manner known to those skilled in the art so as to give a controlled release, for example rapid release or sustained release, of the compounds of the present invention. Pharmaceutically acceptable carriers suitable for use in such compositions are well known in the art. The compositions of the invention may contain 0.1-99% by weight of active compound. The compositions of the invention are generally prepared in unit dosage form. Preferably, a unit dose comprises the active ingredient in an amount of 0.001 to 100 mg. The excipients used in the preparation of these compositions are the excipients known in the art.

Appropriate dosage levels may be determined by any suitable method known to one skilled in the art. It will be understood, however, that the specific dose level for any particular patient will depend upon a variety of factors including the activity of the specific compound employed, the age, body weight, general health, sex, diet, time of administration, route of administration, rate of excretion, drug combination and the severity of the condition to be treated. Preferably, the active agent is administered at a frequency of 1 to 4 times per day. A typical daily dosage is 1 to 1000 µg, e.g. 10 to 500 µg.

Compositions for oral administration include known pharmaceutical forms for such administration, for example lozenges, pastilles, dispersible tablets, powders or granules or as a liquid for spraying into the mouth. Compositions intended for oral use may be prepared according to any method known to the art for the manufacture of pharmaceutical compositions, and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example corn starch or alginic acid; binding agents, for example starch gelatin, acacia, microcrystalline cellulose or polyvinyl pyrrolidone; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time-delay material such as glyceryl monostearate or glyceryl distearate may be employed.

For oral administration, the composition may be in any form that will release the active agent, when held in the mouth, whether for a short time or for a matter of hours. It may be malleable and non-disintegrating, and/or chewable or dispersible. Preferred examples of such compositions are gums, as well as wafers and dispersible tablets (described above). A flavorant will typically be included. It is particularly desirable if the flavorant has mucolytic properties. An example of such a flavorant is menthol.

Aqueous suspensions contain the active materials in admixture with excipients suitable for the manufacture of aqueous suspensions. Such excipients are suspending agents, for example sodium carboxymethylcellulose, methylcellulose. hydroxypropylmethylcellulose, sodium alginate, polyvinyl pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, polyoxyethylene hydrogenated castor oil, fatty acids such as oleic acid, or in a mineral oil such as liquid paraffin or in other surfactants or detergents. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin, or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid, find use in the preparation of injectables.

The or each active agent may be administered together with a mucolytic agent such as menthol. Menthol or another oil, e.g. eucalyptus oil, may be used to make the formulation more palatable.

The following study provides evidence of the utility of the present invention.

Study

The study examined the effects of clonidine and oxybutynin on saliva production in 9 healthy male volunteers. This was an open-label, non-randomised, two-period, rising dose study.

The subjects were assessed on each dosing occasion for saliva production pre-dose and 1 h, 2.5 h, 4 h and 6 h post-dose. Vital signs were recorded at specified times during each study period and adverse events were reported throughout.

For each subject, the maximum % reduction in saliva production compared to placebo was calculated for each dose level. Using this information, a mixed effects regression analysis of the % reduction in saliva versus dose with subject as a random effect was performed for both clonidine and oxybutynin. From this model, an approximate $ED_{30}$ and an $ED_{50}$ were calculated. The doses that gave the best approximate reduction of 30% ($ED_{30}$) in salivary flow was then used as a combination treatment. The mean maximum % reduction in saliva production compared to placebo was also plotted by dose.

Results

No severe or serious adverse events were reported. The most commonly occurring adverse events were headache and fatigue. There were no clinically significant changes to the biochemistry, haematology or urinalysis results observed during the study. There were no clinically significant changes to the vital signs (including blood pressure), physical examination or 12 lead ECGs observed during the study.

Figure 2:
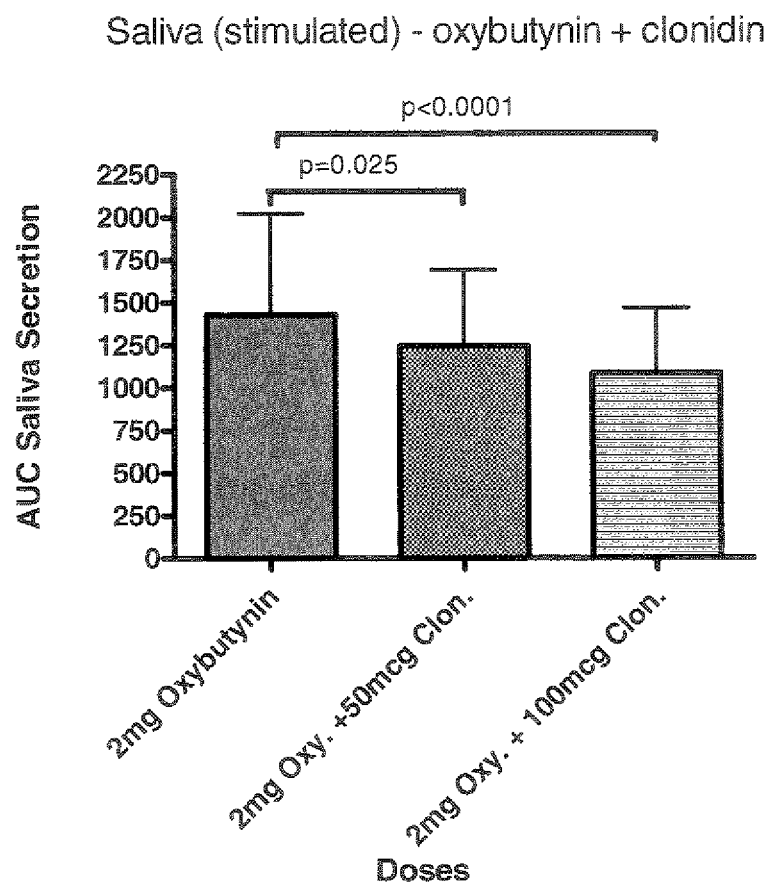

The key observation in this study is based on the Saxon test. See Kohler & Winter, Arthritis Rheum. (1985) 28:1128-32, and Stevens et at, Am. J. Diseases Children (1990) 144:570-571. These results are represented in FIGS. 1 and 2.

The results show a trend towards a reduction in saliva production over time, following administration of oxybutynin and clonidine alone. This effect was most pronounced following administration of clonidine and was significant with increasing dose levels. Likewise, there was a reduction in AUCTs following administration of 50 mcg and 100 mcg clonidine when compared to placebo. There were no significant effects of dose on saliva production following administration of oxybutynin, but the AUCT was reduced following administration of 10 mg when compared to placebo. The ability of oxybutynin to reduce saliva production was more pronounced following administration in combination with clonidine. A reduction in saliva production was observed when the AUCT following administration of placebo was compared to the AUCT following administration of a combination of (i) 2 mg oxybutynin and 50 mcg clonidine or (ii) 2 mg oxybutynin and 100 mcg clonidine. Likewise, a combination of oxybutynin and clonidine resulted in a significant reduction in the AUCT when 2 mg oxybutynin was compared to a combination of (i) 2 mg oxybutynin and 50 mcg clonidine and (ii) a combination of 2 mg oxybutynin and 100 mcg clonidine.

The invention claimed is:

1. A product comprising a therapeutic amount of the α2-adrenoreceptor agonist clonidine and a therapeutic amount of the anti-muscarinic agent oxybutynin, as a combined preparation for separate, simultaneous or sequential use in the treatment of sialorrhoea wherein the amount of clonidine and oxybutynin is synergistically effective in reducing saliva as compared to clonidine or oxybutynin used alone.

2. The product of claim 1 which is formulated as a gum, spray, pastille, lozenge or dispersible tablet.

3. The product of claim 1 wherein the product additionally comprises a mucolytic agent.

4. The product of claim 1 wherein the product additionally comprises menthol or eucalyptus oil.

5. The product of claim 1, wherein the amount of clonidine and oxybutynin is synergistically effective in reducing saliva in a dose-saliva reduction relationship.

6. The product of claim 5, wherein the amount of clonidine is about 30 mcg to about 100 mcg in a single dose, and the amount of oxybutynin is about 2 mg to about 10 mg in a single dose.

* * * * *

UNITED STATES PATENT AND TRADEMARK OFFICE
CERTIFICATE OF CORRECTION

PATENT NO. : 8,481,583 B2
APPLICATION NO. : 12/279217
DATED : July 9, 2013
INVENTOR(S) : Alan Geoffrey Roach et al.

Page 1 of 1

It is certified that error appears in the above-identified patent and that said Letters Patent is hereby corrected as shown below:

On the Title Page, Item (54) and in the Specification, Column 1, Line 2, in the Title:

"CLONIDIN" should read --CLONIDINE--

Signed and Sealed this
Thirty-first Day of December, 2013

Margaret A. Focarino
*Commissioner for Patents of the United States Patent and Trademark Office*

UNITED STATES PATENT AND TRADEMARK OFFICE
CERTIFICATE OF CORRECTION

Page 1 of 1

PATENT NO. : 8,481,583 B2
APPLICATION NO. : 12/279217
DATED : July 9, 2013
INVENTOR(S) : Roach et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this
Sixteenth Day of December, 2014

Michelle K. Lee
*Deputy Director of the United States Patent and Trademark Office*